United States Patent
Kiprijanova et al.

(10) Patent No.: US 9,446,099 B2
(45) Date of Patent: Sep. 20, 2016

(54) METHOD FOR BRAIN CANCER THERAPY BY CO-ADMINISTRATION OF A PARVOVIRUS AND INTERFERON-GAMMA

(75) Inventors: Irina Kiprijanova, Heidelberg (DE); Manuel Fischer, Neckargemuend (DE); Jean Rommelaere, Heidelberg (DE); Joerg Schlehofer, Leimen (DE); Karsten Geletneky, Heidelberg (DE)

(73) Assignees: Deutsches Krebsforschungszentrum Stiftung des Oeffentlichen Rechts, Heidelberg (DE); Ruprecht-Karls-Universitaet Heidelberg, Heidelberg (DE)

(*) Notice: Subject to any disclaimer, the term of this patent is extended or adjusted under 35 U.S.C. 154(b) by 0 days.

(21) Appl. No.: 13/376,150

(22) PCT Filed: May 19, 2010

(86) PCT No.: PCT/EP2010/003070
§ 371 (c)(1),
(2), (4) Date: Apr. 26, 2012

(87) PCT Pub. No.: WO2010/139401
PCT Pub. Date: Dec. 9, 2010

(65) Prior Publication Data
US 2012/0213734 A1    Aug. 23, 2012

(30) Foreign Application Priority Data
Jun. 4, 2009 (EP) .................................. 09007433

(51) Int. Cl.
*A61K 38/21* (2006.01)
*A61K 35/768* (2015.01)

(52) U.S. Cl.
CPC ........... *A61K 38/217* (2013.01); *A61K 35/768* (2013.01); *C12N 2750/14332* (2013.01)

(58) Field of Classification Search
CPC ............. A61K 38/217; A61K 35/768; A61K 2300/00; C12N 2750/14332
See application file for complete search history.

(56) References Cited

U.S. PATENT DOCUMENTS 5,952,221 A    9/1999 Kurtsman et al.
2004/0029106 A1    2/2004 Samulski et al.

FOREIGN PATENT DOCUMENTS

WO    WO 00/22151    4/2000

OTHER PUBLICATIONS

Angelova, A.L, et al. Improvement of gemcitabine-based therapy of pancreatic carcinoma by means of oncolytic parvovirus H-1PV. Clin. Cancer Res., 2009, vol. 15(2), p. 511-519.*
Rommelaere J, et al. Oncolytic parvoviruses as cancer therapies. Cytokine Growth Factor Rev., 2010, vol. 21, p. 185-195.*
Geletneky, K. et al. Complete remission of advanced autologous intracranial gliomas by oncolytic parvovirus H-1. European Journal of Cancer Supplements, 2005, vol. 3, No. 2, Abstract 186.*
Nathalia Geise et al., Suppression of metastatic hemangiosarcoma by a parvovirus MVMp vector transducing the IP-10 chemokine into immunocopetent mice:, Cancer Gene Therapy, May 2002, vol. 9, No. 5, pp. 432-442, XP002554188.
Andreas Haag et al., "Highly efficient transduction and expression of cytokine genes inhuman tumor cells by means of automous parvovirus vectors: generation of antitumor responses in recipient mice", Human Gene Therapy, vol. 11, No. 4, Mar. 1, 2000, pp. 597-609, XP0025541889.
M. Ederlin et al., "TNF-alpha and the IFN-gamma-inducible protein 10 (IP-10/CXCL-10) delivered by parvoviral vectors act in synergy to induce antitumor effects in mouse glioblastoma" Cancer Gene Therapy, vol. 16. No. 2, Feb. 2009, pp. 149-160, XP002554228.
Abschuetz Anette et al., "Oncolytic murine autonomous parvovirus, a candidate vector for glioma gene therapy, is innocuous to normal and immunocompetent mouse glial cells", Cell and Tissue Research, vol. 325, No. 3, May 3, 2006, p. 423-436, XP 019428267.
Assia Angelova et al., Oncolytic rat parvovirus H-iPV, a candidate for the treatment of human lymphoma: In vitro and in vivo studies, Molecular Therapy: The Journal of the American Society of Gene Therapy, Jul. 2009, vol. 17, No. 7, Apr. 14, 2009, p. 1164-1172, XP009125443.
M. Ehtesham et al., "Treatment of intracranial glioma with in situ interferon-gamma and tumor necrosis factor-alpha gene transfer", Cancer Gene Therapy, Nov. 1, 2002, vol. 9, No. 11, pp. 925-934, XP002599007.
International Search Report for PCT/EP2010/003070.

* cited by examiner

*Primary Examiner* — Robert Landsman
*Assistant Examiner* — Bruce D Hissong
(74) *Attorney, Agent, or Firm* — Crowell & Moring LLP

(57) ABSTRACT

Described is a pharmaceutical composition comprising (a) a parvovirus and (b) a cytokine, preferably IFN-γ, and the use of said composition for treatment of cancer, e.g., a brain tumor.

4 Claims, 2 Drawing Sheets

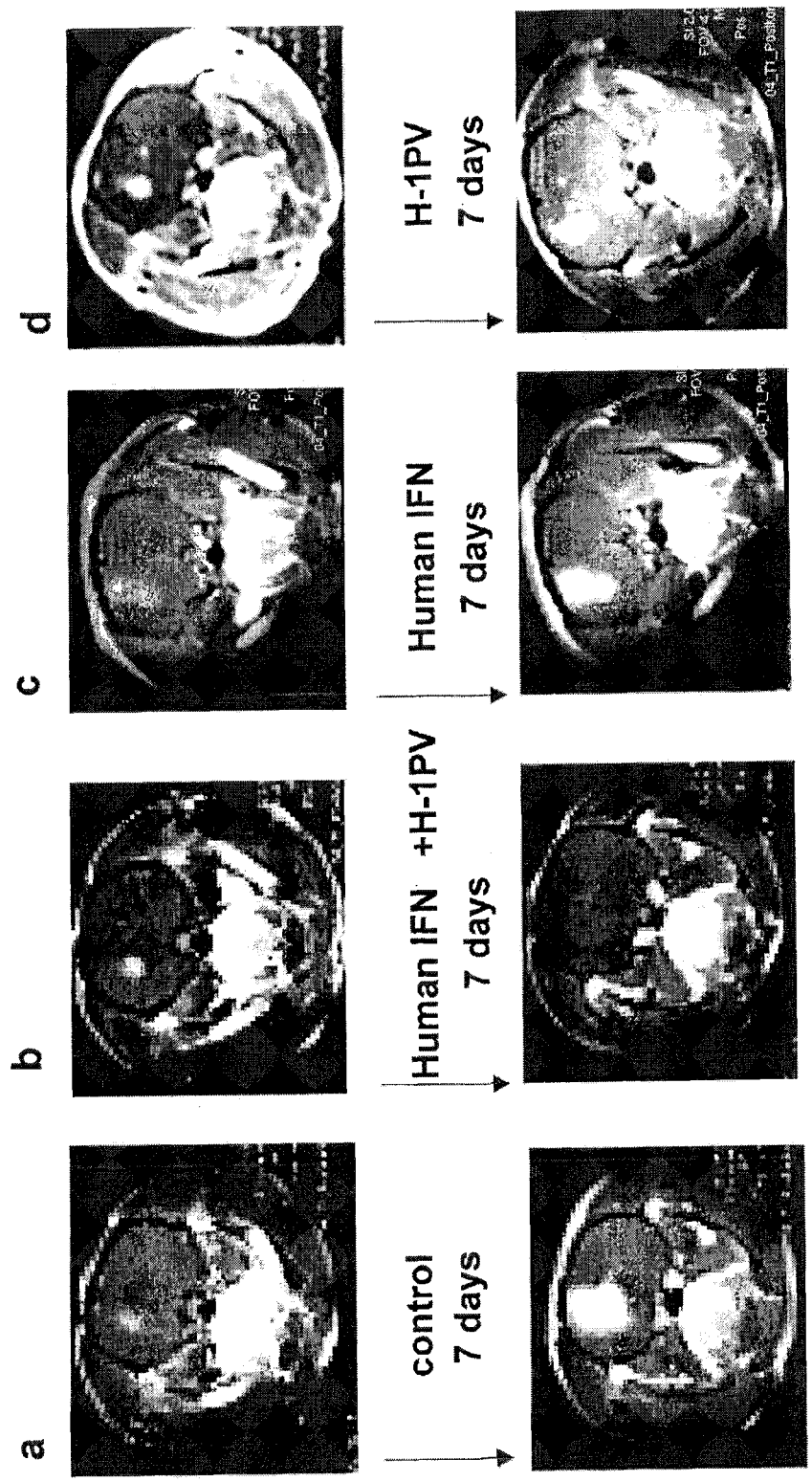

METHOD FOR BRAIN CANCER THERAPY BY CO-ADMINISTRATION OF A PARVOVIRUS AND INTERFERON-GAMMA

This application is a national stage of PCT International Application No. PCT/EP2010/003070; filed May 19, 2010, which claims priority under 35 U.S.C. §119 to European Application No. 09007433.7, filed Jun. 4, 2009, the entire disclosure of which is herein expressly incorporated by reference.

The present invention relates to a pharmaceutical composition comprising (a) a parvovirus and (b) a cytokine, preferably IFN-γ, and the use of said composition for treatment of cancer, e.g., a brain tumor.

Malignant human gliomas account for the largest number of human malignant brain tumors. So far, the treatment of gliomas includes neurosurgical techniques (resection or stereotactic procedures), radiation therapy and chemotherapy. However, despite these therapies gliomas are considered as incurable as they fail to respond to ionising radiation, chemotherapy and surgical resection. In other words, with these therapies only a very limited prolongation of lifespan of patients can be achieved, i.e. despite these therapies, the average life span after diagnosis is merely 12 to 16 months.

Cancer therapy using viruses or armed vector derivatives that specifically kill neoplastically transformed cells (oncolysis) is a novel approach to the treatment of this lethal disease. Some autonomous parvoviruses belong to the category of so called oncolytic viruses. Parvoviruses are small (25-30 nm) non-enveloped particles containing a 5.1 kb single-stranded DNA genome from which two nonstructural (NS1, NS2) and two capsid (VP1, VP2) proteins are expressed. Parvovirus H-1PV has the unique advantage of triggering a distinct death process, at least in brain and some other tumors, namely the cytosolic relocation and activation of lysosomal proteases (cathepsins). Several members of the parvovirus genus (H-1PV, MVM, LuIII), whose natural hosts are rodents, are presently under consideration for cancer gene therapy applications due to their failure to transform host cells, capacity for asymptomatic infection of humans, and ability to preferentially propagate in (oncotropism) and kill (oncolysis) neoplastically transformed cells. MVMp and H-1PV viruses have been shown to exert oncosuppressive activities in vivo, i.e. they are able to inhibit the formation of spontaneous, chemically or virally induced tumors in laboratory animals. Vectors based on a parvoviral expression cassette retain the oncotropic features of the wild type viruses. Despite the impressive results achieved, the anticancer efficacy of the most promising parvovirus candidates for human clinical applications (including H-1PV) needs to be improved, e.g., as regards the extension of life span after diagnosis.

Therefore, it is the object of the present invention to provide means for an improved parvovirus-based therapy.

According to the invention this is achieved by the subject matters defined in the claims. The present invention is based on the applicant's findings that by the combined treatment with a parvovirus and a cytokine such as IFN-γ the therapeutic efficiency can be improved. The observation that the combination of H-1PV and IFN-γ also shows beneficial effects on immunodeficient mammals indicates that this effect does not depend on T cells.

BRIEF DESCRIPTION OF THE DRAWINGS

FIG. 2: Monitoring of human tumor (U 87 glioma) growth by MR imaging

Figure 1:
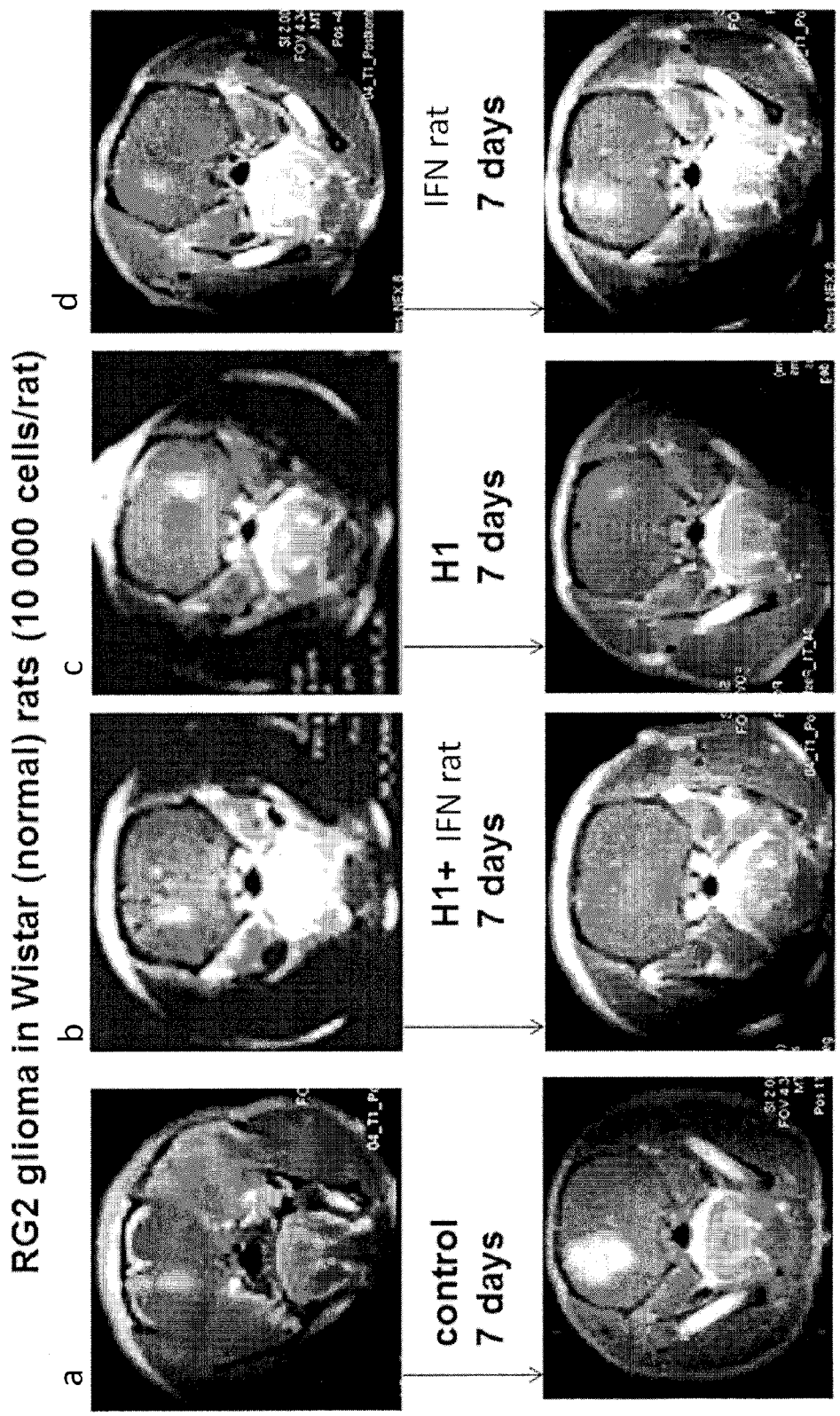
FIG. 1: Monitoring of rat tumor (RG2 glioma) growth by MR imaging

Thus, the present invention provides a pharmaceutical composition containing a (a) parvovirus and (b) a cytokine, preferably (a) a parvovirus and (b) a cytokine as separate entities, e.g. in separate containers.

As used herein, the term "cytokine" relates to a category of signalling molecules that are used extensively in cellular communication. They comprise proteins, peptides, or glycoproteins. The term cytokine encompasses a large family of polypeptide regulators that are produced widely throughout the body by cells of diverse embryological origin. The action of cytokines may be autocrine, paracrine, and endocrine. All cytokines are critical to the development and functioning of both the innate and adaptive immune response. They are often secreted by immune cells that have encountered a pathogen, thereby activating and recruiting further immune cells to increase the system's response to the pathogen. Relying on the assays shown in Examples 2 and 3 the person skilled in the art is in a position to select cytokines that show beneficial effects when administrated according to the present invention.

Preferably, the cytokine of the present invention is an interferon. All interferons (IFNs) are natural cell-signalling proteins produced by the cells of the immune system of most vertebrates in response to challenges such as viruses, parasites and tumor cells. Interferons are produced by a wide variety of cells in response to the presence of double-stranded RNA, a key indicator of viral infection. Interferons assist the immune response by inhibiting viral replication within host cells, activating natural killer cells and macrophages, increasing antigen presentation to lymphocytes, and inducing the resistance of host cells to viral infection. All interferons in general have several effects in common and, accordingly, the results obtained by use of IFN-γ in combination with H1-PV might apply to further interferons. Interferons are antiviral and possess antioncogenic properties, macrophage and natural killer cell activation, and enhancement of major histocompatibility complex glycoprotein classes I and II, and thus presentation of foreign (microbial) peptides to T cells. The production of interferons is induced in response to microbes such as viruses and bacteria and their products (viral glycoproteins, viral RNA, bacterial endotoxin, bacterial flagella, CpG sites), as well as mitogens and other cytokines, for example interleukin 1, interleukin 2, interleukin-12, tumor necrosis factor and colony-stimulating factor, that are synthesised in the response to the appearance of various antigens in the body. Their metabolism and excretion take place mainly in the liver and kidneys. They rarely pass the placenta but they can cross the blood-brain barrier.

There are three major classes of interferons that have been described for humans:

(a) Interferon type I: The type I interferons present in humans are IFN-α, IFN-β and IFN-ω.
(b) Interferon type II: In humans this is IFN-γ.
(c) Interferon type III: Signal through a receptor complex consisting of IL10R2 (also called CRF2-4) and IFNLR1 (also called CRF2-12)

In a more preferred embodiment of the present invention, the interferon is interferon-γ.

Preferably, in said pharmaceutical composition the parvovirus and the cytokine are present in an effective dose and combined with a pharmaceutically acceptable carrier. "Pharmaceutically acceptable" is meant to encompass any carrier, which does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc.. Such carriers can be formulated by conventional methods and can be administered to the subject at an effective dose.

An "effective dose" refers to amounts of the active ingredients that are sufficient to affect the course and the severity of the disease, leading to the reduction or remission of such pathology. An "effective dose" useful for treating and/or preventing these diseases or disorders may be determined using methods known to one skilled in the art (see for example, Fingl et al., The Pharmocological Basis of Therapeutics, Goodman and Gilman, eds. Macmillan Publishing Co., New York, pp. 1-46 ((1975)).

Preferred doses for the parvovirus are in the range of about $10^8$ to $10^9$ pfu (single injection) and for the cytokine, in particular IFN-$\gamma$, in the range of about $10^6$ to $10^7$ U (single injection).

Additional pharmaceutically compatible carriers can include gels, bioasorbable matrix materials, implantation elements containing the therapeutic agent, or any other suitable vehicle, delivery or dispensing means or material(s).

Administration of the compounds may be effected by different ways, e.g. by intravenous, intraperetoneal, subcutaneous, intramuscular, topical or intradermal administration. The route of administration, of course, depends on the kind of therapy and the kind of compounds contained in the pharmaceutical composition. A preferred route of administration is intravenous administration. The dosage regimen of the parvovirus and the cytokine is readily determinable within the skill of the art, by the attending physician based on patient data, observations and other clinical factors, including for example the patient's size, body surface area, age, sex, the particular parvovirus to be administered, the time and route of administration, the tumor type and characteristics, general health of the patient, and other drug therapies to which the patient is being subjected.

If the parvovirus comprises infectious virus particles with the ability to penetrate through the blood-brain barrier, treatment can be performed or at least initiated by intravenous injection of the parvovirus, e.g., H1 virus. A preferred route of administration is intratumoral administration.

Since long-term intravenous treatment is susceptible to becoming inefficient as a result of the formation of neutralizing antibodies to the parvovirus, different modes of administration can be adopted after an initial regimen intravenous viral administration, or such different administration techniques, e.g., intracranial or intratumoral virus administration, can be alternatively used throughout the entire course of parvoviral treatment.

As another specific administration technique, the parvovirus (virus, vector and/or cell agent) containing composition can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvovirus containing composition to be injected locally at various times without further surgical intervention. The parvovirus or derived vectors containing composition can also be injected into the tumor by stereotactic surgical techniques or by neuronavigation targeting techniques.

Administration of the parvovirus containing compositions can also be performed by continuous infusion of viral particles or fluids containing viral particles through implanted catheters at low flow rates using suitable pump systems, e.g., peristaltic infusion pumps or convection enhanced delivery (CED) pumps.

As yet another method of administration of the parvovirus containing composition is from an implanted article constructed and arranged to dispense the parvovirus containing composition to the desired cancer tissue. For example, wafers can be employed that have been impregnated with the parvovirus containing composition, e.g., parvovirus H1, wherein the wafer is attached to the edges of the resection cavity at the conclusion of surgical tumor removal. Multiple wafers can be employed in such therapeutic intervention. Cells that actively produce the parvovirus, e.g., parvovirus H1, or H1 vectors, can be injected into the tumor, or into the tumoral cavity after tumor removal.

The combined therapy according to the invention is useful for the therapeutic treatment of cancer, in particular brain tumors and can significantly improve the prognosis of said diseases. Parvovirus H1 infection effects killing of tumor cells but does not harm normal cells and such infection can, for example, be carried out by intracerebral use of a suitable parvovirus, e.g., parvovirus H1 (-1PV), or a related virus or vectors based on such viruses, to effect tumor-specific therapy without adverse neurological or other side effects.

The present invention also relates to the use of (a) a parvovirus and (b) a cytokine, preferably IFN-$\gamma$, for the preparation of a pharmaceutical composition for the treatment of cancer wherein, preferably, (a) and (b) are sequentially (or separately) administered.

In one preferred embodiment of the present invention, the combination of agents is utilized in the treatment of brain tumors such as glioma, medulloblastoma and meningioma. Preferred gliomas are malignant human glioblastomas. However, the therapy according to the present invention is, in principle, applicable to any tumor that can be infected with the parvovirus, e.g., parvovirus H1. Such tumors comprise pancreatic tumors, prostate tumors, lung tumors, renal tumors, liver tumors, lymphoma, breast cancer and hepatoma.

The term "parvovirus" as used herein comprises wild-type or modified replication-competent derivatives thereof, as well as related viruses or vectors based on such viruses or derivatives. Suitable parvoviruses, derivatives, etc. as well as cells which can be used for actively producing said parvoviruses and which are useful for therapy, are readily determinable within the skill of the art based on the disclosure herein, without undue empirical effort.

In another preferred embodiment of the present invention, the parvovirus of the composition includes parvovirus H1 (H1-PV) or a related parvovirus such as LuIII, Mouse minute virus (MMV), Mouse parvovirus (MPV), Rat minute virus (RMV), Rat parvovirus (RPV) or Rat virus (RV).

Patients treatable by the combination of agents according to the invention include humans as well as non-human animals. Examples of the latter include, without limitation, animals such as cows, sheep, pigs, horses, dogs, and cats.

Preferably, the parvovirus and the cytokine are administered as separate compounds. The administration of the cytokine, when administered separately, can be accomplished in a variety of ways (see above) including systemically by the parenteral and enteral routes.

In a further preferred embodiment, the parvovirus is administered together with the cytokine.

The below examples explain the invention in more detail.

EXAMPLE 1

Materials and Methods (A) Virus Production and Detection

Wild type H-1 virus was produced by infecting NBK cells, purified by Iodixanol gradient centrifugation and dialyzed against Ringer solution. Virus titers were determined as previously described and expressed as replication center-forming units (cfu). Briefly, serial dilutions of purified viruses were applied to NBK cells. At 48 hours post infection, infected cultures were blotted onto filters and replication centers were detected by hybridization, using a virus DNA-specific radioactive probe (Russell et al., *J Virol* 1992;66:2821-8).

(B) Animal Studies (i) Anaesthesia. All surgical and imaging procedures were performed under gaseous anaesthesia with isoflurane (Aerrane®, Baxter, Maurepas, France) in pure oxygen. Isoflurane concentrations varied between 5% for the initiation of anaesthesia to 2% (±0.5%) during the surgical or imaging procedure.

(ii) Animals. 6 to 7 weeks old female Wistar rats or immunodeficient RNU rats (Charles River, Sulzfeld, Germany) weighing 220-250 g were used for tumor cell implantation. Wistar rats were implanted with RG-2 glioma cells and RNU-rats were implanted with human U87 cells. Animals were kept under conventional conditions (temperature 22±2° C., relative humidity 55±10%, dark-light rhythm of 12 hr) with unrestricted access to a balanced pellet diet and water. Animal experiments were performed according to the French and European Community directives for animal care (number 86/609/EEC of Nov. 24, 1986).

(C) Magnetic Resonance Imaging

The animals were examined in a 2.45 Tesla MRI scanner (Bruker, Ettlingen, Germany) using T1 weighted imaging before and after injection of 0.4 ml contrast medium (Gadodiamide, Omniscan™ Amersham, Braunschweig, Germany) into the tail vein. Gadodiamide-enhanced T1 imaging was performed 5 min after injection. During MR examination, rats were anaesthetized by Isoflurane insufflations (initial dose 5%, maintenance 2%). Tumor volumes were determined using MRIcro software.

EXAMPLE 2

Increasing of Treatment Efficiency of Rat Glioma in Immunocompetent Rats by Combining IFN-γ with Parvovirus H-1 (H-1PV)

Tumor model: Cells of a rat glioma cell line (RG2 cells) were implanted ($10^4$ cells per animal) intracranially in the right forebrain of Wistar rats. In total, 11 immunocompetent Wistar rats (6-7 weeks old, 240-250 g, female) were analyzed in the experiments.

3 animals were used as controls, i.e. tumor cells were implanted but not followed by any treatment, and tumor growth was monitored by MR imaging. 8 animals were divided in three groups:

(a) One group (3 rats, bearing rat glioma tumors) was treated by i.v. injection of IFN-γ (recombinant rat IFN-γ, $10^5$ U per animal), 7 days after tumor cell implantation.

(b) The second group (3 rat glioma bearing rats) was treated by i.v. injection of a combination of H-1PV and rat IFN-γ, 7 days after tumor implantation (final dose of H-1PV per animal: $10^8$ pfu; final concentration of IFN-γ per animal: $10^5$ U).

(c) The third group (2 rat glioma bearing rats) was treated by i.v. injection of H-1PV alone ($10^8$ pfu per animal), 7 days after tumor implantation.

Tumor growth was analyzed by MR imaging at intervals of 7 days.

Results:

The results are shown in FIG. 1.

(a) In all control animals, tumors grew continuously, and rats were sacrificed after a maximum of 14 days because of signs of suffering (cachexia, weakening, and difficulty in moving or eating).

(b) Complete tumor regression after 7 days post treatment was observed in 2 rats, in the group treated with the combination of H-1PV and rat IFN-γ. Tumor growth in one animal ceased after treatment.

(c) In the group of animals treated with H-1PV alone, the tumor volume was reduced 7 days after infection, (not completely regressed at this time point).

(d) The tumors in rats, treated only with IFN-γ, continued to grow after treatment but not as fast as in control animals. The rats from this group survived to a maximum of 19 days after tumor cell implantation (i.e. 5 days longer compared to control animals). Neither tumor regression nor arrest of tumor growth was observed in this group.

It can be expected that not only additive but even synergistic effects can be achieved in vivo by the combined treatment with H-1PV and a cytokine such as IFN-γ.

EXAMPLE 3

Increasing of Treatment Efficiency of Human Glioma Cell Line-derived Brain Tumor in Immunodeficient Rats by Combining IFN-γ with Parvovirus H-1 (H-1PV)

Tumor model: Cells of a human glioma cell line (U87 cells) were implanted ($10^5$ cells per animal) intracranially in the right forebrain of the rats. In total, 18 immunodeficient RNU rats (6-7 weeks old, 220-250 g, female) were analyzed in the experiments.

Five animals were used as controls, i.e. tumor cells were implanted but not subject to any treatment, and tumor growth was monitored by MR imaging. The remaining 13 animals were divided in three treatment groups:

(a) One group (5 rats, bearing human glioma cell-derived tumors) were treated by i.v. injection of IFN-γ (recombinant human IFN-γ, $10^5$ U per animal), 7 days after tumor cell implantation.

(b) The second group (5 human glioma bearing rats) was treated by i.v. injection of a combination of H-1PV and human IFN-γ, 7 days after tumor implantation (final dose of H-1PV per animal: $10^8$ pfu; final concentration of IFN-γ per animal: $10^5$ U).

(c) The third group (3 rats) was treated with i.v. injection of H-1PV alone ($10^8$ pfu per animal), 7 days after tumor implantation.

Tumour growth was analyzed by MR imaging at intervals of 4 days.

Results:

The results are shown in FIG. 2.

(a) In all control animals, tumors grew continuously, and rats were sacrificed after a maximum of 14 days because of signs of suffering (cachexia, weakening, difficulty in moving or eating).

(b) Complete human tumor regression was observed in 3 rats, in the group treated with the combination of H-1PV and human IFN-γ. Tumor growth in two animals ceased after treatment, and tumor volume remained constant until rats were sacrificed for histological analysis.

(c) The tumors in rats, treated only with IFN-γ, continued to grow after treatment but not as fast as in control animals. The rats from this group survived to a maximum of 3 weeks post tumor cell implantation (i.e. one week longer compared to control animals). Neither tumor regression nor arrest of tumor growth was observed in this group.

(d) In the group of animals treated with H-1PV alone, the tumour volume was reduced 7 days after infection (but not completely regressed at this time point).

The invention claimed is:

1. A method of treating cancer, comprising the sequential administration of a parvovirus and IFN-γ, wherein the parvovirus is H1 (H1-PV) and wherein the cancer is a brain tumor.

2. The method of claim 1, wherein the brain tumor is a glioma, medulloblastoma or meningioma.

3. The method of claim 2, wherein the glioma is a malignant human glioblastoma.

4. The method of claim 1, wherein the parvovirus is administered by intratumoral administration.

* * * * *